(12) United States Patent
Kuo

(10) Patent No.: US 12,345,617 B2
(45) Date of Patent: Jul. 1, 2025

(54) GAS DETECTION DEVICE WITH SELF PROTECTION FUNCTIONALITY

(71) Applicant: Welmade Technology Corporation, Phoenix, AZ (US)

(72) Inventor: Yi-Nan Kuo, Hsinchu (TW)

(73) Assignee: WELMADE TECHNOLOGY CORPORATION, Phoenix, AZ (US)

( * ) Notice: Subject to any disclaimer, the term of this patent is extended or adjusted under 35 U.S.C. 154(b) by 342 days.

(21) Appl. No.: 17/952,982

(22) Filed: Sep. 26, 2022

(65) Prior Publication Data

US 2024/0102892 A1 Mar. 28, 2024

(51) Int. Cl.
*G01N 1/20* (2006.01)
*G01N 1/14* (2006.01)

(52) U.S. Cl.
CPC ............. *G01N 1/2035* (2013.01); *G01N 1/14* (2013.01); *G01N 2001/1445* (2013.01); *G01N 2001/205* (2013.01)

(58) Field of Classification Search
None
See application file for complete search history.

(56) References Cited

FOREIGN PATENT DOCUMENTS

| CN | 207263711 U | * | 4/2018 | |
| CN | 209549690 U | * | 10/2019 | ............. B02C 23/04 |

* cited by examiner

*Primary Examiner* — John E Breene
*Assistant Examiner* — Nigel H Plumb
(74) *Attorney, Agent, or Firm* — Muncy, Geissler, Olds & Lowe, P.C.

(57) ABSTRACT

A gas detection device is provided, including: a first inlet channel, a second inlet channel, a detection module, a switch valve and a control module. The first inlet channel is configured to input a sample gas. The detection module is configured to obtain a detected concentration value of a detection target from the sample gas. The switch valve is switchable to communicate the detection module with the first inlet channel or the second inlet channel. The control module is communicative with the detection module and the switch valve and includes a processing unit and a setting unit. The setting unit is configured to set a setting concentration value, and the processing unit controls the switch valve according to the detected concentration value and the setting concentration value so as to protect the detection module. Therefore, the gas detection device has self-protection functionality.

13 Claims, 8 Drawing Sheets

GAS DETECTION DEVICE WITH SELF PROTECTION FUNCTIONALITY

BACKGROUND OF THE INVENTION

Field of the Invention

The present invention relates to a gas detection device.

Description of the Prior Art

In the process of manufacturing semiconductors, airborne molecular contaminants (AMC) may be generated, such as volatile organic compounds (VOCs), fluorocarbon, or the like. Specifically, VOCs and fluorocarbon may damage to human health and environment. Therefore, monitoring of the air condition in the clean room is important to avoid inhaling toxic substances and harmful gas emissions.

However, a conventional gas detection device has poor detection accuracy when the concentration of the detection target is too high, which may cause by detainment of the detection target and is easy to damage the gas detection device. In addition, the conventional gas detection device is fixedly arranged in the clean room, which requires a large space for arrangement and is inconvenient to be moved.

The present invention is, therefore, arisen to obviate or at least mitigate the above-mentioned disadvantages.

SUMMARY OF THE INVENTION

The main object of the present invention is to provide a gas detection device, which has self-protection function and provides good detection accuracy.

To achieve the above and other objects, the present invention provides a gas detection device, including: a first inlet channel, a second inlet channel, a detection module, a switch valve and a control module. The first inlet channel is configured to input a sample gas. The second inlet channel is configured to input a purge gas. The detection module is configured to obtain at least one detected concentration value of at least one detection target from the sample gas. The switch valve is connected respectively with the first inlet channel, the second inlet channel and the detection module, and the switch valve is switchable between a sampling position and a purging position to communicate the detection module with one of the first inlet channel and the second inlet channel. The control module is communicative respectively with the detection module and the switch valve and includes a processing unit and a setting unit. The setting unit is configured to set at least one setting concentration value, and the processing unit controls the switch valve according to the at least one detected concentration value and the at least one setting concentration value.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
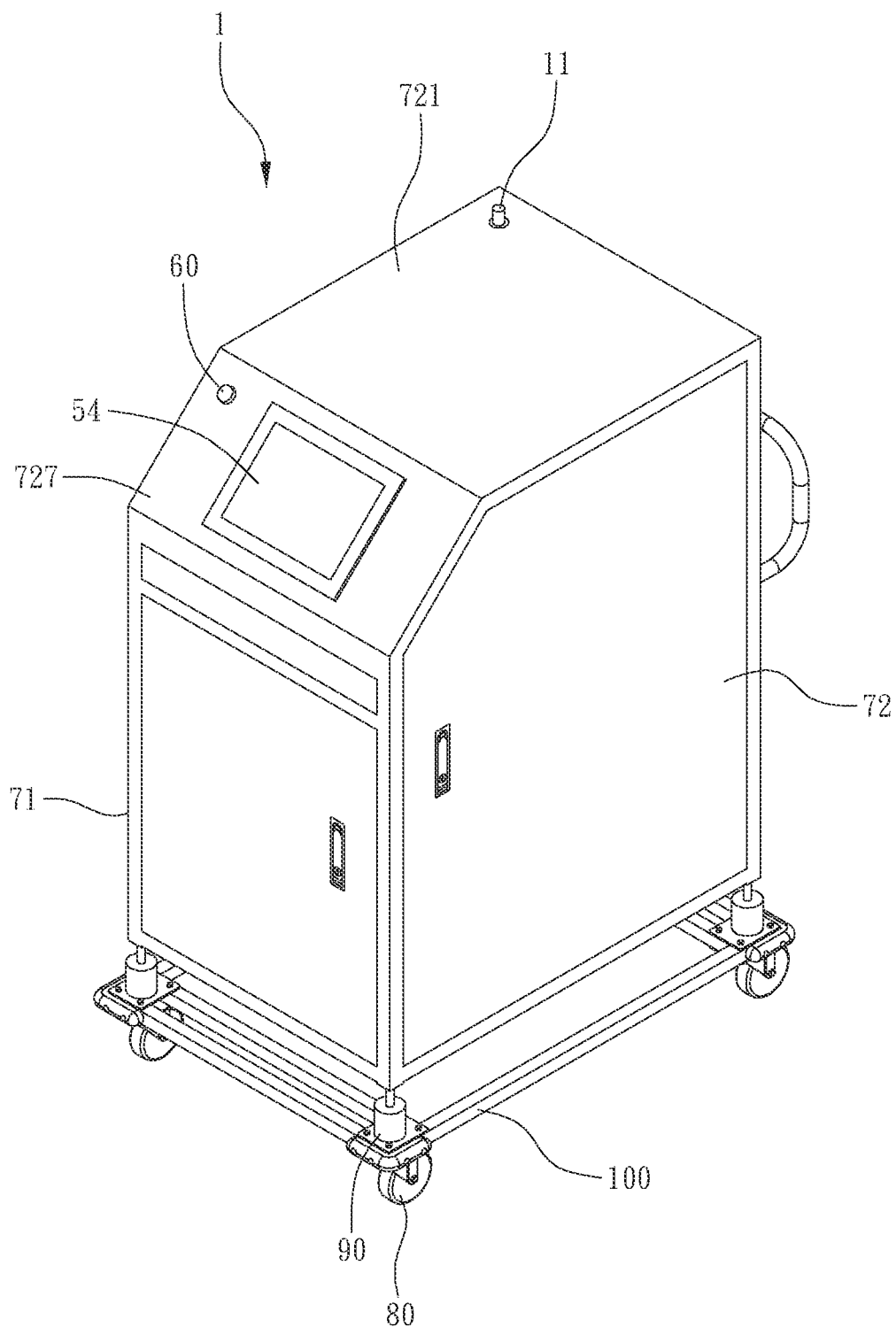
FIGS. 1-3 are stereograms of a preferable embodiment of the present invention as viewed from different sides.
Figure 2:
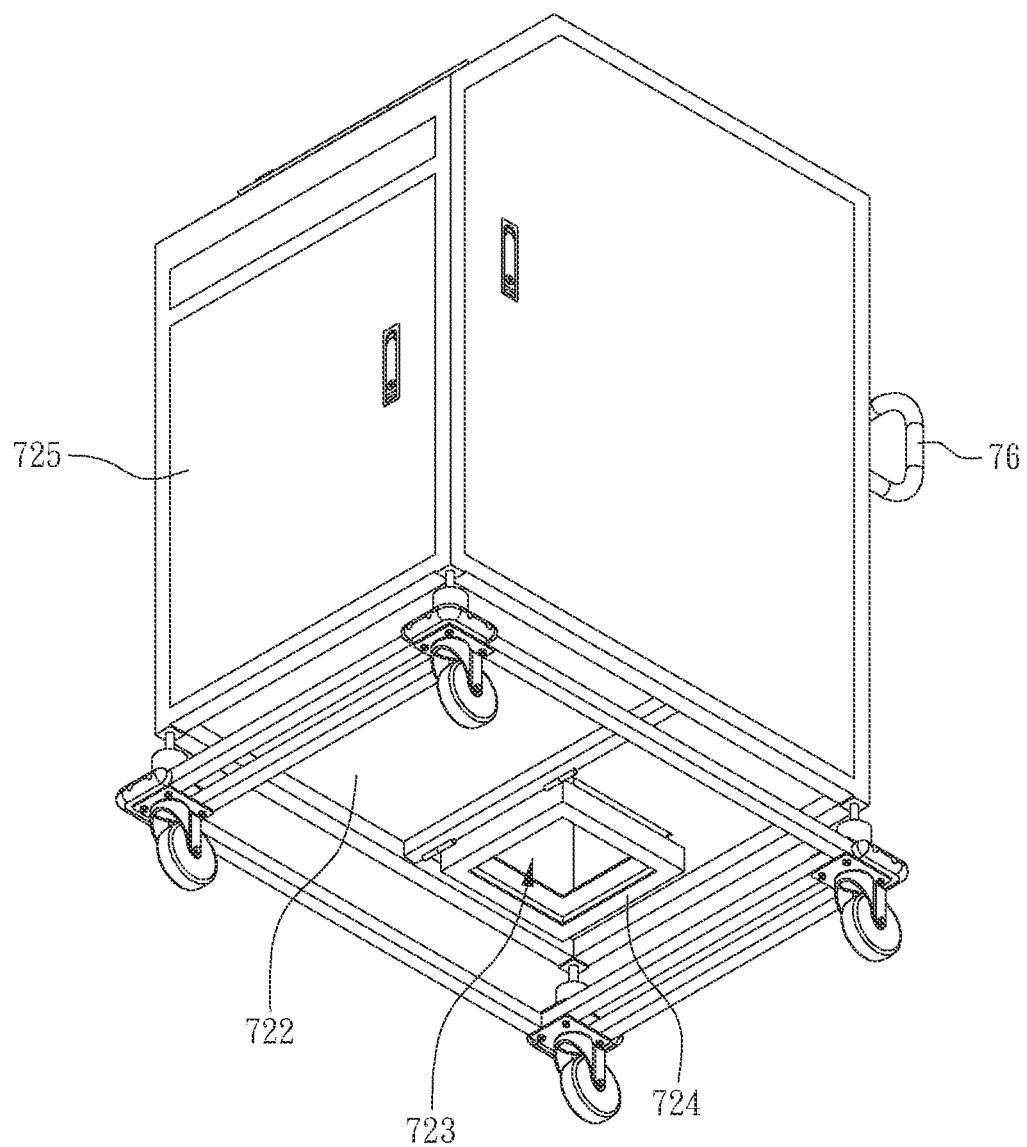

Please refer to FIGS. 1 to 8 for a preferable embodiment of the present invention. A gas detection device 1 of the present invention includes a first inlet channel 10, a second inlet channel 20, a detection module 30, a switch valve 40 and a control module 50.

The first inlet channel 10 is configured to input a sample gas. The second inlet channel 20 is configured to input a purge gas. The detection module 30 is configured to obtain at least one detected concentration value of at least one detection target from the sample gas. The switch valve 40 is connected respectively with the first inlet channel 10, the second inlet channel 20 and the detection module 30, and the switch valve 40 is switchable between a sampling position and a purging position to communicate the detection module 30 with one of the first inlet channel 10 and the second inlet channel 20. The control module 50 is communicative respectively with the detection module 30 and the switch valve 40 and includes a processing unit 51 and a setting unit 52. The setting unit 52 is configured to set at least one setting concentration value, and the processing unit 51 controls the switch valve 40 according to the at least one detected concentration value and the at least one setting concentration value so as to protect the detection module 30 and have good detection accuracy.

Figure 6:
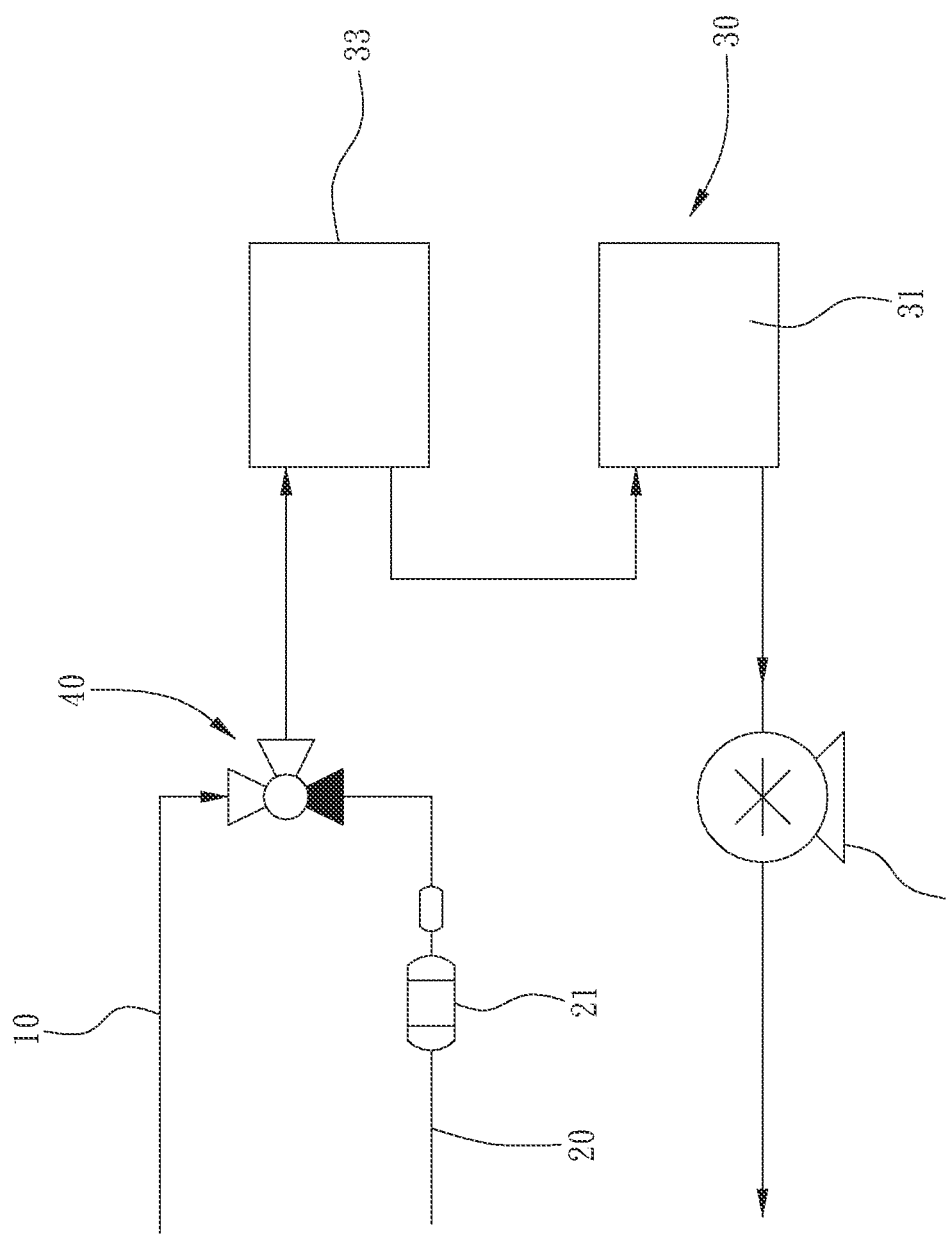
FIG. 6 is a drawing showing a flow path of a sample gas according to a preferable embodiment of the present invention.
Figure 7:
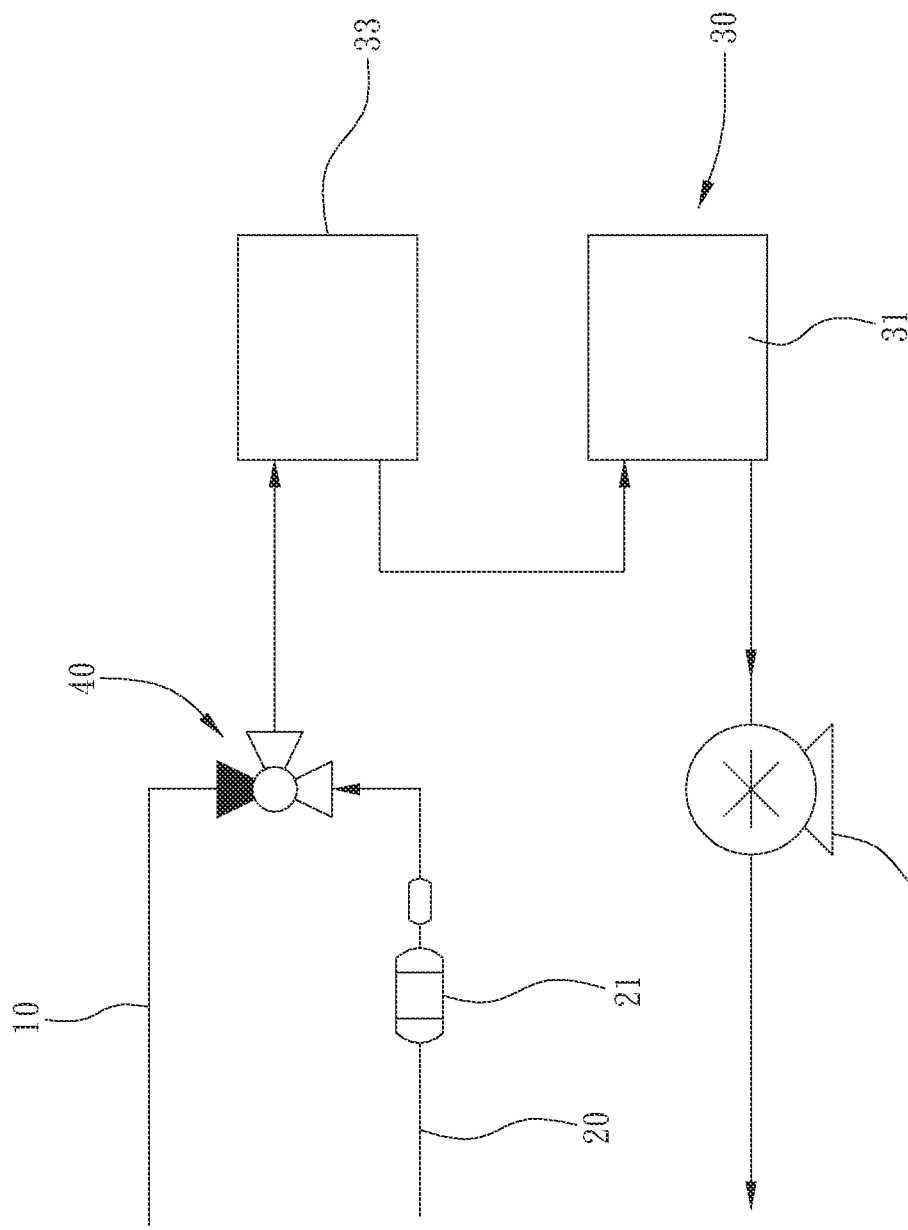
FIG. 7 is a drawing showing a flow path of a purge gas according to a preferable embodiment of the present invention.

Specifically, as shown in FIG. 6, the switch valve 40 is normally in the sampling position to communicate the first inlet channel 10 with the detection module 30 for detection. When the at least one detected concentration value is higher than the at least one setting concentration value, the processing unit 51 controls the switch valve 40 to be switched to the purging position, and the second inlet channel is communicated with the detection module 30, which allows the purge gas to flow through chambers and channels of the detection module 30 for cleaning so as to protect the detection module 30, as shown in FIG. 7. Preferably, the second inlet channel 20 includes at least one gas filter 21 disposed thereon, and the at least one gas filter 21 includes a disposable filter unit so as to filter the purge gas. The purge gas may be clean air, nitrogen, carbon dioxide, or the like, and the setting concentration value may be set according to different requirements. The at least one gas filter 21 may also include a charcoal filter or any other types of filters according to requirements.

The detection module 30 includes a detector 31 and a pump 32 connected with the detector 31, and the pump 32 helps to discharge the gas in the detector 31 for next detection. In this embodiment, the detection module 30 further includes a converter 33 communicated with the detector 31, and the converter 33 is configured to heat the sample gas to form the at least one detection target; the detector 31 is a laser gas analyzer which provides fast respond, high sensitivity and high accuracy. In other embodiments, the detector may be another type of analyzer or the detection module may include two or more detectors for detection of multiple said detection targets.

The gas detection device 1 further includes an indicating unit 60 communicative with the control module 50, and the indicating unit 60 includes at least one of a lighting member 61, a speaker and a displayer 62. When the at least one detected concentration value is higher than the at least one setting concentration value, the processing unit 51 controls the indicating unit 60 to change an operational state. For example, the lighting member 61 is flashing or changed color when the at least one detected concentration value is higher than the at least one setting concentration value; and the at least one detected concentration value is flashily displayed on the displayer 62.

Figure 4:
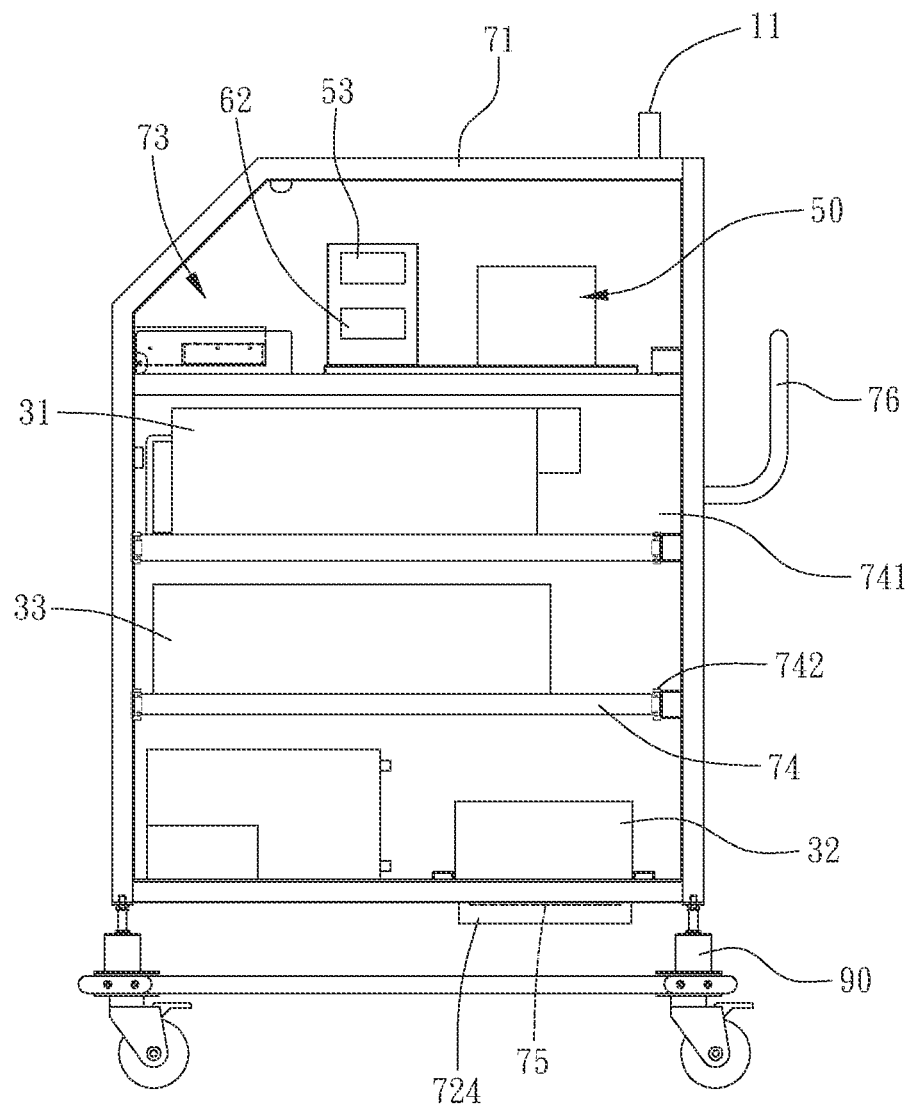
FIG. 4 is a side view of a preferable embodiment of the present invention when a board is removed from a frame.

The gas detection device 1 further includes a rack 70, and the rack 70 includes a frame 71 and a plurality of boards 72 assembled to the frame 71. The frame 71 and the plurality of boards 72 define a receiving space 73 therebetween, and the detection module 30, the switch valve 40 and the control module 50 are received within the receiving space 73 and integrated with the rack 70, as shown in FIG. 4, which has a small volume and is convenient to be moved. Preferably, the rack 70 further includes a plurality of plates 74 connected to the frame 71, the plurality of plates 74 divide the receiving space 73 into a plurality of receiving regions 741, and at least one of the plurality of plates 74 is drawable from the receiving space 73. In this embodiment, a part of the plurality of plates 74 is connected with the frame 71 by slide rails 742 so as to be easy to draw out and arrange related components; and at least one of the plurality of plates 74 has a plurality of penetrating holes 743 disposed therethrough so as to provide heat dissipation effect and be convenient to assemble the related components. The gas detection device 1 further includes a temperature sensor 53, and the temperature sensor 53 is configured to sense a temperature in the receiving space 73 so as to avoid failure of the components disposed in the receiving space 73 due to high temperature.

Moreover, the plurality of boards 72 include a top board 721 and a bottom board 722 disposed on two opposite sides of the frame 71. An inlet 11 of the first inlet channel 10 protrudes out of the receiving space 73 through the top board 721, and an inlet 21 of the second inlet channel 20 protrudes out of the receiving space 73 through one of the plurality of boards 72 different from the top board 721 so as to avoid interference between the sample gas and the purge gas. The pump 32 is disposed on the bottom board 722, and a filter 75 (such as a high efficiency particulate air filter, HEPA) is disposed on an outer side of the bottom board 722 and corresponds to at least one opening 723 disposed on the bottom board 722 so as to facilitate heat dissipation, filter the gas discharged through the at least one opening 723 and avoid air pollution. In this embodiment, the outer side of the bottom board 722 has a cover 724 pivotally disposed thereon and covering the at least one opening 723, and the filter 75 is arranged between the cover 724 and the bottom board 722, which is convenient to replace. In other embodiments, the filter may be disposed on an inner side of the bottom board or received within the at least one opening.

The plurality of boards 72 further include a front board 725 and a rear board 726 disposed on two opposite sides of the frame 71, and the rear board 726 has a plurality of through holes 726a disposed thereon so as to dissipate heat out of the receiving space 73. In this embodiment, a tube 22 having the second inlet channel 20 disposed therein penetrates through one of the plurality of through holes 726a and the inlet 21 of the second inlet channel 20 is located out of the receiving space 73. Specifically, the plurality of boards 72 further include an inclined board 727 disposed between the top board 721 and the front board 725, and the lighting member and a monitor 54 are disposed on the inclined board 727. The monitor 54 is communicative with the control module 50, which is convenient to use. However, the monitor may be replaced by an operation display interface for easy operation.

Figure 5:
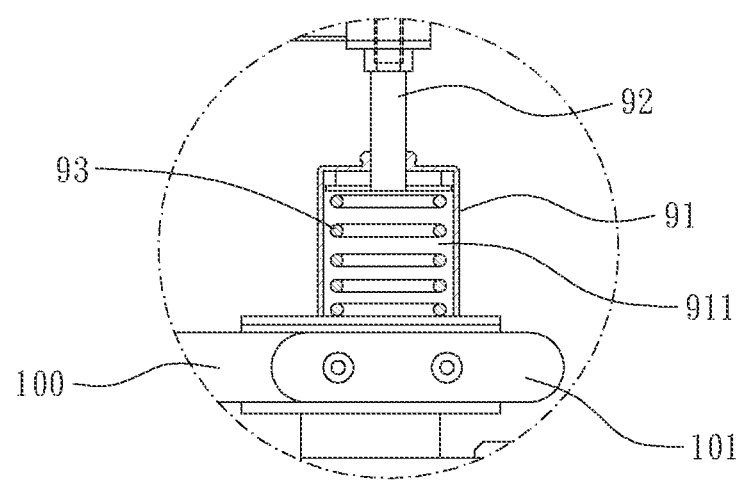
FIG. 5 is a partial cross-sectional enlargement according to a preferable embodiment of the present invention.

The gas detection device 1 further includes a plurality of casters 80 and a plurality of cushioning units 90, and each of the plurality of cushioning units 90 is disposed between the rack 70 and one of the plurality of casters 80 and includes a base 91 having a hollow portion 911 disposed therein, a connection member 92 and an elastic member 93. The connection member 92 is connected to the rack 70 and partially penetrates within the hollow portion 911, and the elastic member 93 is received in the hollow portion 911 and abutted against and between the connection member 92 and the base 91, as shown in FIG. 5. Therefore, the gas detection device 1 is easy to move and the plurality of cushioning units 90 provide good cushioning effect to the components disposed therein. Preferably, the gas detection device 1 further includes a supporting frame 100, and the supporting frame 100 is connected between the plurality of casters 80 and the plurality of cushioning units 90 so that the plurality of casters 80 and the plurality of cushioning units 90 are stably restricted to the supporting frame 100 for stable assembling and good structural strength. An outer contour of the supporting frame 100 is larger than an outer contour of the rack 70 and is a circumferentially closed polygon; and a plurality of bumpers 101 are disposed on an outer surface of the supporting frame 100 so as to avoid unexpected collision. The plurality of bumpers 101 may be made of plastic, rubber, foaming material, or the like.

Figure 3:
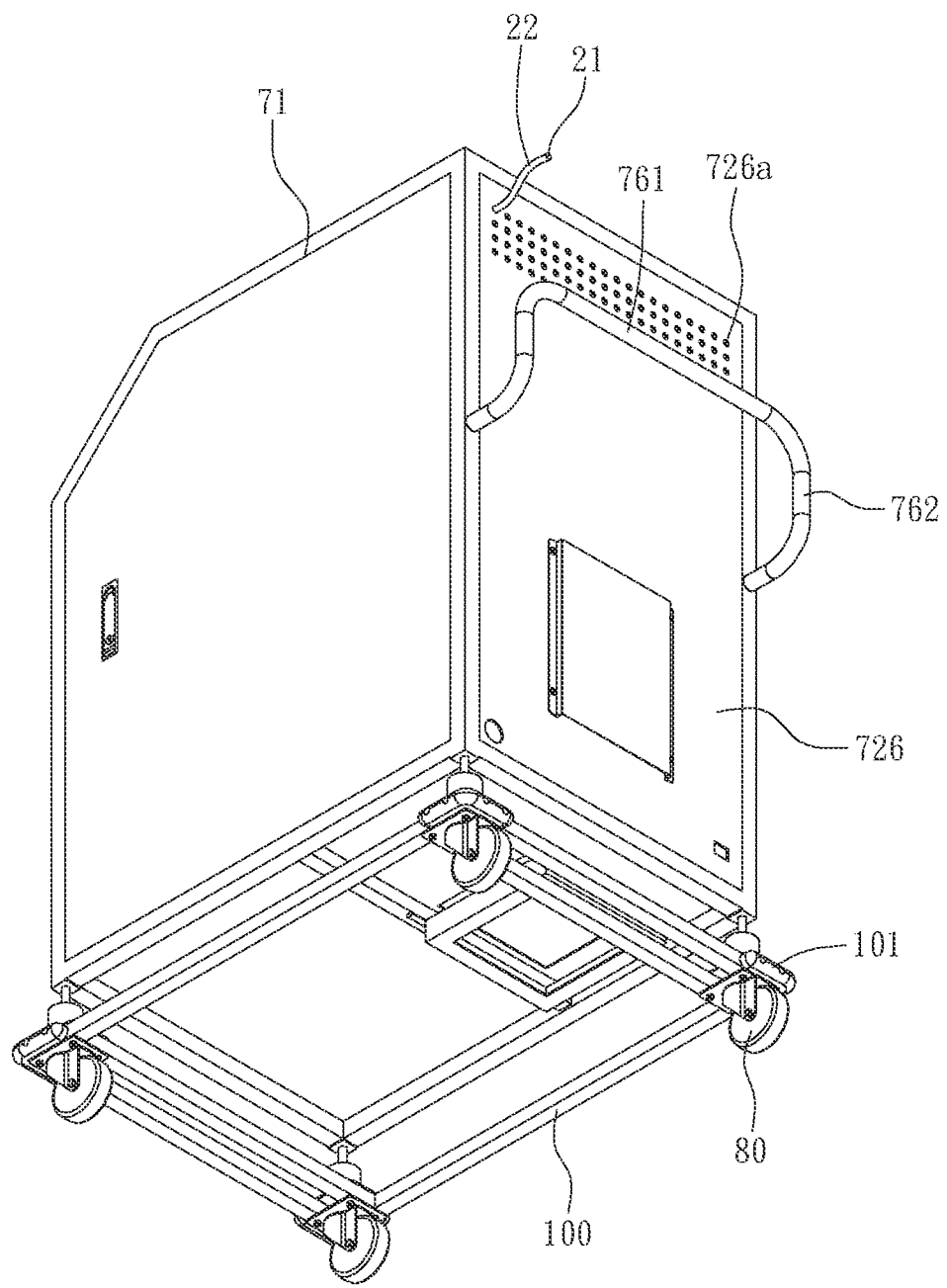

The rack 70 further includes a handle bar 76 connected to the frame 71, and the handle bar 76 includes a handling portion 761 and two arms 762 extending from two opposite sides of the handling portion 761. One end of each of the two arms 762 is connected to a middle portion of the frame 71 located between the top board 721 and the bottom board 722, and the two arms 762 curvedly extend and are located below the handling portion 761, as shown in FIGS. 3 and 4, which is convenient to push or pull the handling portion 761 and provides labor saving effect.

Figure 8:
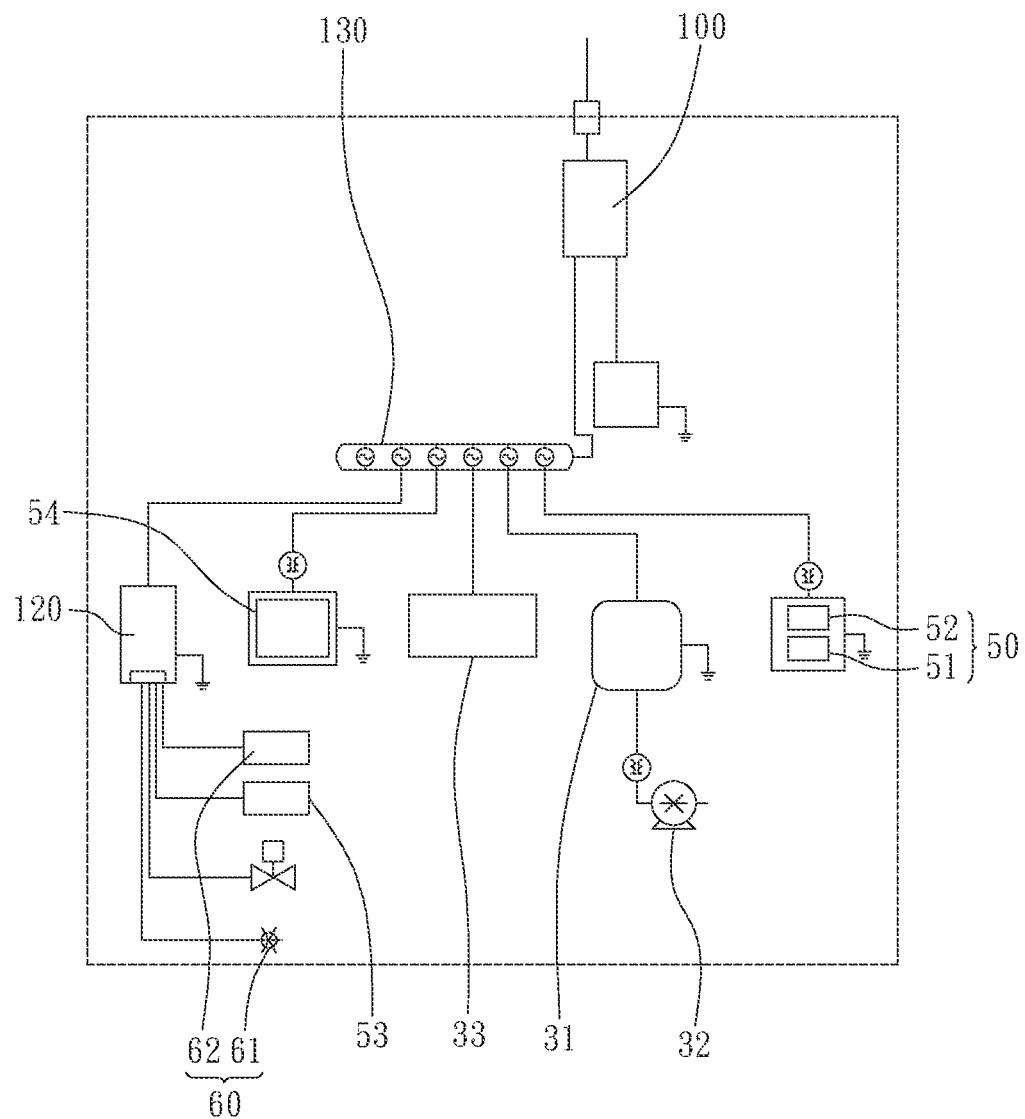
FIG. 8 is a line diagram of a preferable embodiment of the present invention.

Please refer to FIG. 8, in this embodiment, the gas detection device 1 further includes a main power supply unit 110, a sub power supply unit 120 and an extension cord 130. The main power supply unit 110 is configured to be connected with an external power source, and the extension cord 130 is electrically connected between the main power supply unit 110 and the sub power supply unit 120. The temperature sensor 53, the indicating unit 60 and the valve 40 are respectively connected to the sub power supply unit 120, and the monitor 54, the converter 33, the detector 31 and the control module 50 are respectively connected to the extension cord 130, which is convenient for power management and arrangement.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A gas detection device, including:
   a first inlet channel, configured to input a sample gas;
   a second inlet channel, configured to input a purge gas;
   a detection module, configured to obtain at least one detected concentration value of at least one detection target from the sample gas;

a switch valve, connected respectively with the first inlet channel, the second inlet channel and the detection module, being switchable between a sampling position and a purging position to communicate the detection module with one of the first inlet channel and the second inlet channel; and a control module, communicative respectively with the detection module and the switch valve, including a processing unit and a setting unit, the setting unit configured to set at least one setting concentration value, the processing unit controlling the switch valve according to the at least one detected concentration value and the at least one setting concentration value;

wherein the gas detection device further includes a rack, the rack includes a frame and a plurality of boards assembled to the frame, the frame and the plurality of boards define a receiving space therebetween, and the detection module, the switch valve and the control module are received within the receiving space.

2. The gas detection device of claim 1, wherein the switch valve is normally in the sampling position to communicate the first inlet channel with the detection module, when the at least one detected concentration value is higher than the at least one setting concentration value, the processing unit controls the switch valve to be switched to the purging position, and the second inlet channel is communicated with the detection module.

3. The gas detection device of claim 1, wherein the second inlet channel includes at least one gas filter disposed thereon.

4. The gas detection device of claim 1, wherein the detection module includes a converter and a detector communicated with each other, and the converter is configured to heat the sample gas to form the at least one detection target.

5. The gas detection device of claim 4, wherein the detector is a laser gas analyzer.

6. The gas detection device of claim 1, further including an indicating unit communicative with the control module, wherein the indicating unit includes at least one of a lighting member, a speaker and a displayer, and when the at least one detected concentration value is higher than the at least one setting concentration value, the processing unit controls the indicating unit to change an operational state.

7. The gas detection device of claim 1, wherein the plurality of boards include a top board and a bottom board disposed on two opposite sides of the frame, an inlet of the first inlet channel protrudes out of the receiving space through the top board, and an inlet of the second inlet channel protrudes out of the receiving space through one of the plurality of boards different from the top board.

8. The gas detection device of claim 7, wherein the detection module includes a detector and a pump connected with the detector, the pump is disposed on the bottom board, and a filter is disposed on the bottom board and corresponds to at least one opening disposed on the bottom board.

9. The gas detection device of claim 1, further including a plurality of casters and a plurality of cushioning units, wherein each of the plurality of cushioning units is disposed between the rack and one of the plurality of casters and includes a base having a hollow portion disposed therein, a connection member and an elastic member, the connection member is connected to the rack and partially penetrates within the hollow portion, and the elastic member is received in the hollow portion and abutted against and between the connection member and the base.

10. The gas detection device of claim 1, further including a plurality of casters, a plurality of cushioning units and a supporting frame, wherein each of the plurality of cushioning units is disposed between the rack and one of the plurality of casters, and the supporting frame is connected between the plurality of casters and the plurality of cushioning units.

11. The gas detection device of claim 1, wherein the rack further includes a plurality of plates connected to the frame, the plurality of plates divide the receiving space into a plurality of receiving regions, and at least one of the plurality of plates is drawable from the receiving space.

12. The gas detection device of claim 1, further including a temperature sensor, wherein the temperature sensor is configured to sense a temperature in the receiving space.

13. The gas detection device of claim 8, wherein the switch valve is normally in the sampling position to communicate the first inlet channel with the detection module, when the at least one detected concentration value is higher than the at least one setting concentration value, the processing unit controls the switch valve to be switched to the purging position, and the second inlet channel is communicated with the detection module; the second inlet channel includes at least one gas filter disposed thereon, and the at least one gas filter includes a disposable filter unit; the detection module includes a converter communicated with thedetector, and the converter is configured to heat the sample gas to form the at least one detection target; the detector is a laser gas analyzer; the gas detection device further includes an indicating unit communicative with the control module, the indicating unit includes at least one of a lighting member, a speaker and a displayer, and when the at least one detected concentration value is higher than the at least one setting concentration value, the processing unit controls the indicating unit to change an operational state; the gas detection device further includes a plurality of casters and a plurality of cushioning units, each of the plurality of cushioning units is disposed between the rack and one of the plurality of casters and includes a base having a hollow portion disposed therein, a connection member and an elastic member, the connection member is connected to the rack and partially penetrates within the hollow portion, and the elastic member is received in the hollow portion and abutted against and between the connection member and the base; the gas detection device further includes a supporting frame, and the supporting frame is connected between the plurality of casters and the plurality of cushioning units; an outer contour of the supporting frame is larger than an outer contour of the rack and is a circumferentially closed polygon; the rack further includes a plurality of plates connected to the frame, the plurality of plates divide the receiving space into a plurality of receiving regions, and at least one of the plurality of plates is drawable from the receiving space; the gas detection device further includes a temperature sensor, the temperature sensor is configured to sense a temperature in the receiving space; the rack further includes a handle bar connected to the frame, the handle bar includes a handling portion and two arms extending from two opposite sides of the handling portion, one end of each of the two arms is connected to a middle portion of the frame located between the top board and the bottom board, and the two arms curvedly extend and are located below the handling portion; and the plurality of boards further include a front board and a rear board disposed on two opposite sides of the frame, and the rear board has a plurality of through holes disposed thereon.

* * * * *